(12) United States Patent
Lovec et al.

(10) Patent No.: US 6,621,005 B1
(45) Date of Patent: Sep. 16, 2003

(54) HERMETIC CABLE SEALING SYSTEM

(76) Inventors: Oliver Lovec, 12270 74th Ave. North, Seminole, FL (US) 33772; Joseph Lovec, 12270 74th Ave. North, St. Petersburg, FL (US) 33772

( * ) Notice: Subject to any disclaimer, the term of this patent is extended or adjusted under 35 U.S.C. 154(b) by 159 days.

(21) Appl. No.: 09/999,423

(22) Filed: Dec. 3, 2001

(51) Int. Cl.$^7$ ............................................... H02G 15/02
(52) U.S. Cl. ................................................... 174/74 R
(58) Field of Search ............................ 174/74 R, 74 A, 174/75 B, 84 R; 600/112, 134; 348/73

(56) References Cited

U.S. PATENT DOCUMENTS

| | | | | |
|---|---|---|---|---|
| 5,739,472 A | * | 4/1998 | Buck et al. | 174/107 |
| 5,868,664 A | * | 2/1999 | Speier et al. | 348/73 |
| 6,030,339 A | * | 2/2000 | Tatsuno et al. | 600/112 |

FOREIGN PATENT DOCUMENTS

JP          7-39515     *   2/1995

* cited by examiner

*Primary Examiner*—Chau N. Nguyen
(74) *Attorney, Agent, or Firm*—Thomas Frost

(57) ABSTRACT

A hermetic cable sealing system for mating an endoscope video cable to a head shell of a camera to produce a hermetic seal between the video cable and the camera so as to prevent any liquid from entering the system during fluid sterilization. The cable sealing system has a cap unit that is designed accept the video cable and a coupler fitting which connects the cap unit to the head shell. The cap unit has a coupling member with a threaded first end, a ribbed second end, and a bend relief member that connects with the ribbed second end. The coupler fitting has a threaded first end configured to mate with the head shell and a threaded second end configured to mate with threaded first end of the coupler member. The first end of the coupler fitting has a setscrew for retaining a cable crimp that is secured to the video cable. At least one square o-ring is positioned between the coupler fitting and the cap unit to produce a hermetic seal. Additionally, an O-ring is positioned between the first and second ends of the coupler fitting to produce a hermetic seal between the coupler fitting and the head shell.

13 Claims, 4 Drawing Sheets

HERMETIC CABLE SEALING SYSTEM

BACKGROUND OF THE INVENTION

1. Field of the Invention

The present invention relates to a hermetic cable sealing system and more particularly pertains to the hermetic sealing of endoscope video cables to a camera while allowing for fluid sterilization as a result of the hermetic seal.

2. Description of the Prior Art

The use of cable retaining and sealing systems of various designs and configurations is known in the prior art. For example, U.S. Pat. No. 5,868,664 which issued to Speier et al. discloses a video camera head configuration for an endoscope having a hermetically sealed inner chamber that facilitates the use of fluid sterilization. The patent also discloses the use of a snap joint which releasably engages a first and second part sealed via an elastomer O-ring and is threadably attached to an optical device.

U.S. Pat. No. 6,080,101 which issued to Tatsuno et al. discloses an endoscopic imaging apparatus having a hermetically sealed cable structure that is attached to an endoscope either directly or via an adapter. The disclosure of this patent also teaches the use of an insulator which can be used to achieve a hermetic seal between an outer metallic sheathing and an internal shielding sheathing. Furthermore, the hermetic sealing structure is capable of being autoclaved.

Another patent of interest is U.S. Pat. No. 6,030,339, which issued to Tatsuno et al., wherein there is disclosed an electrical optical adapter unit that detachably connects a camera cable to an endoscope head. It is hermetically sealed to permit autoclaving and is thus watertight. The adapter unit also has an anti-breaking member for preventing breakage of the camera cable.

U.S. Pat. No. 6,053,639 which issued to Chen discloses an optic fiber inner tube connector having a hollow tubular body that is threadably attached to an inner tube containing a sealing ring.

Another pertinent prior art patent is U.S. Pat. No. 5,980,450 which issued to Thompson and which discloses a coupler for coupling a scope with an imaging instrument having a body that includes a first end adapted to mate with the scope and a second end adapted to mate with the imaging instrument, as well as a sheath that is hermetically sealed to the coupler.

U.S. Pat. No. 4,611,888, which issued to Prenovitz et al., discloses a device for coupling an endoscope and a video camera having a sealing means which enables the endoscope to be completely immersed in a liquid sterilization bath through the use of multiple O-rings.

U.S. Pat. No. 4,601,497, which issued to Bartholomew, is also of interest as disclosing a swivelable connection assembly for tubular conduits, and having an elastomeric ring-like seal and a threaded connection end.

Lastly, Japanese Patent Number 10258034 A, which issued to Tatsuno et al., discloses a photographing apparatus for an endoscope having a hermetic seal part that provides for a watertight structure.

While all of the inventions described in the above patents fulfill their respective particular objectives and requirements, none of the aforementioned patents illustrate or describe a hermetic cable sealing system that allows for the hermetic sealing of endoscope video cables to a camera while allowing for fluid sterilization as a result of a created hermetic seal. The aforementioned patents also make no provisions for an endoscope video cable hermetic sealing system which is threadably attachable to a head shell and which also has a rigid cap snap fitted to a flexible member, nor one that is hermetically sealed to the head shell through a specific O-ring configuration in combination with a tiered threaded fitting which retains a video cable by a set screw.

In this respect, the hermetic cable sealing system according to the present invention substantially departs from the conventional concepts and designs of the prior art, and in doing so provides an apparatus primarily developed for the purpose of providing hermetic sealing of endoscope video cables to a camera while allowing for fluid sterilization as a result of the created hermetic seal.

Therefore, it can be appreciated that there exists a continuing need for a. new and improved hermetic cable sealing system which can be used for the hermetic sealing of endoscope video cables to a camera while allowing for fluid sterilization as a result of an established hermetic seal. In this regard, the present invention substantially fulfills this need.

SUMMARY OF THE INVENTION

In view of the foregoing disadvantages inherent in the known types of cable retaining and sealing systems of various designs and configurations now present in the prior art, the present invention provides an improved hermetic cable sealing system. As such, the general purpose of the present invention, which will be described subsequently in greater detail, is to provide a new and improved hermetic cable sealing system, and method of assembly and use, which has all the advantages of the prior art cable sealing systems and none of the disadvantages.

To attain this, the present invention essentially comprises a hermetic cable sealing system for mating an endoscope video cable to a camera. The cable sealing system has a cap unit and a coupler fitting. The cap unit is adapted to internally accept the video cable. The cap unit includes both a rigid elongated coupling member and an elongated flexible member. The elongated coupling member has internally threaded first and second ends. The second end has at least one rib extending radially outwardly therefrom. The elongated flexible member has at least one internal slot for retaining the rib of the coupling member, and is also adapted to accept the second end of the coupling member. The coupler fitting is adapted to mate the cap unit to the camera, and is provided with an externally threaded first end and an externally threaded second end. The externally threaded first end of the coupler fitting is configured to mate with the internally threaded first end of the coupling member of the cap unit. At least one O-ring is used to seal the threaded second end of the coupler fitting with the threaded first end of the coupling member of the cap unit. The externally threaded first end of the coupler fitting is configured to mate with a head shell of the camera. The threaded first end of the coupler fitting is adapted to accept a setscrew which retains the video cable in position. The coupler fitting has at least one outer O-ring retained between the threaded first end and the threaded second end which is adapted to seal the coupler fitting to the head shell of the camera.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description only and should not be regarded as limiting the scope and intent of the invention.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved hermetic cable sealing system which has all of the advantages of the prior art cable retaining and sealing systems and none of the disadvantages.

It is another object of the present invention to provide a new and improved hermetic cable sealing system which may be easily and efficiently manufactured and marketed.

It is further object of the present invention to provide a new and improved hermetic cable sealing system which is of a durable and reliable construction.

An even further object of the present invention is to provide a new and improved hermetic cable sealing system which is susceptible of a low cost of manufacture with regard to both materials and labor, and which accordingly is then susceptible of low prices of sale to the consuming public, thereby making such hermetic cable sealing systems economically available to the buying public.

Even still another object of the present invention is to provide a hermetic cable sealing system for the hermetic sealing of endoscope video cables to a camera while allowing for fluid sterilization as a result of the created hermetic seal.

Lastly, it is an object of the present invention to provide a new and improved hermetic cable sealing system for mating an endoscope video cable to a head shell of a camera, thereby to produce a hermetic seal between the video cable and the camera for preventing any liquid. from entering the system during fluid sterilization.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
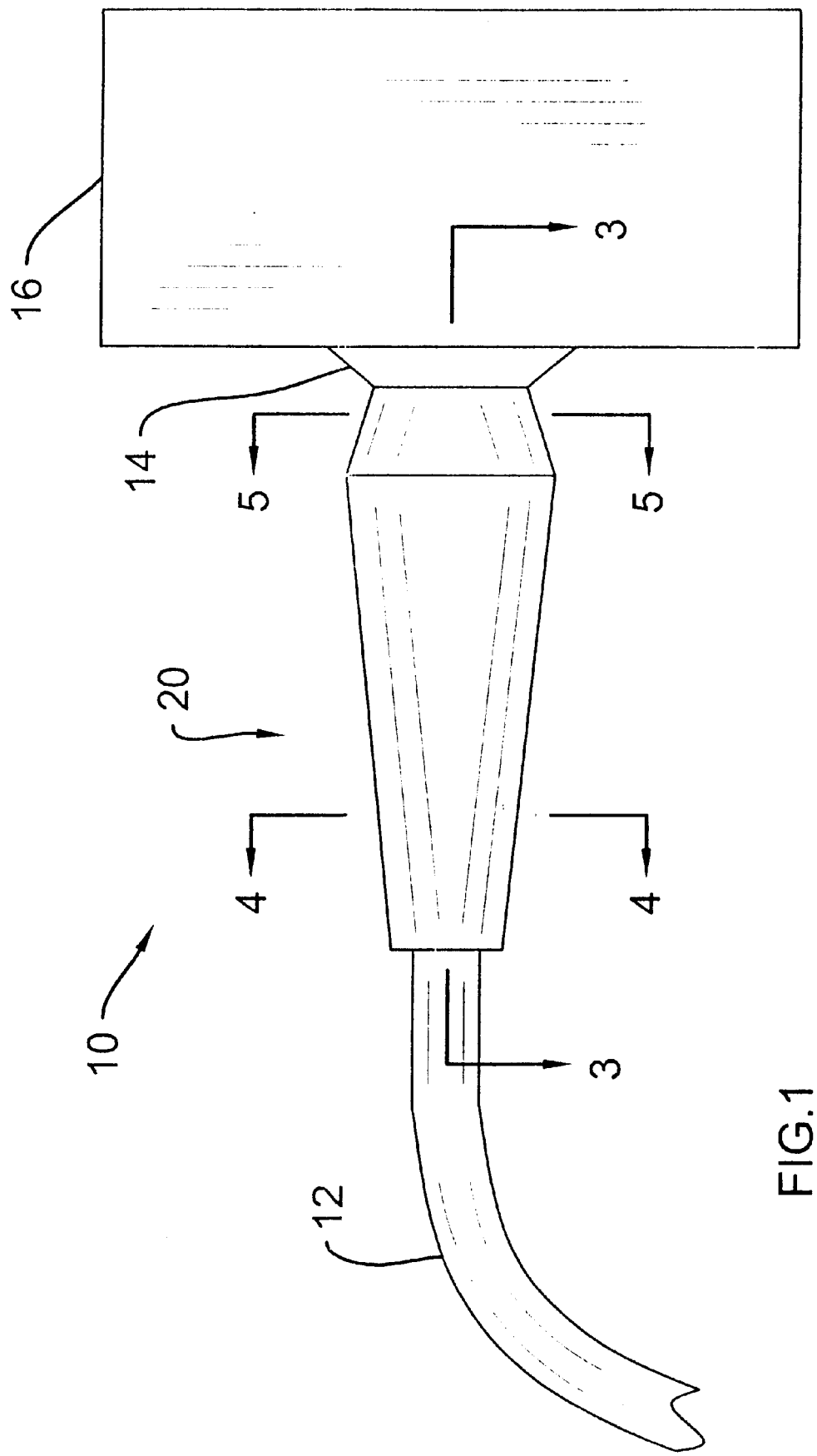
FIG. 1 is a front elevation view of the preferred embodiment of the hermetic cable sealing system constructed in accordance with the principles of the present invention.

With reference now to the drawings, and in particular to FIG. 1 thereof, a new and improved hermetic cable sealing system 10 for hermetically sealing an endoscope video cable 12 to a head shell 14 of a camera 16, while allowing for fluid sterilization as a result of the hermetic seal will be described. More particularly, the hermetic cable sealing system 10 has a cap unit 20 which is threadably attached to the head shell 14 to produce a flush sealed connection. This connection will produce a watertight seal between the cap unit 20 and the head shell 14 so as to protect the internal components during fluid sterilization.

Figure 2:
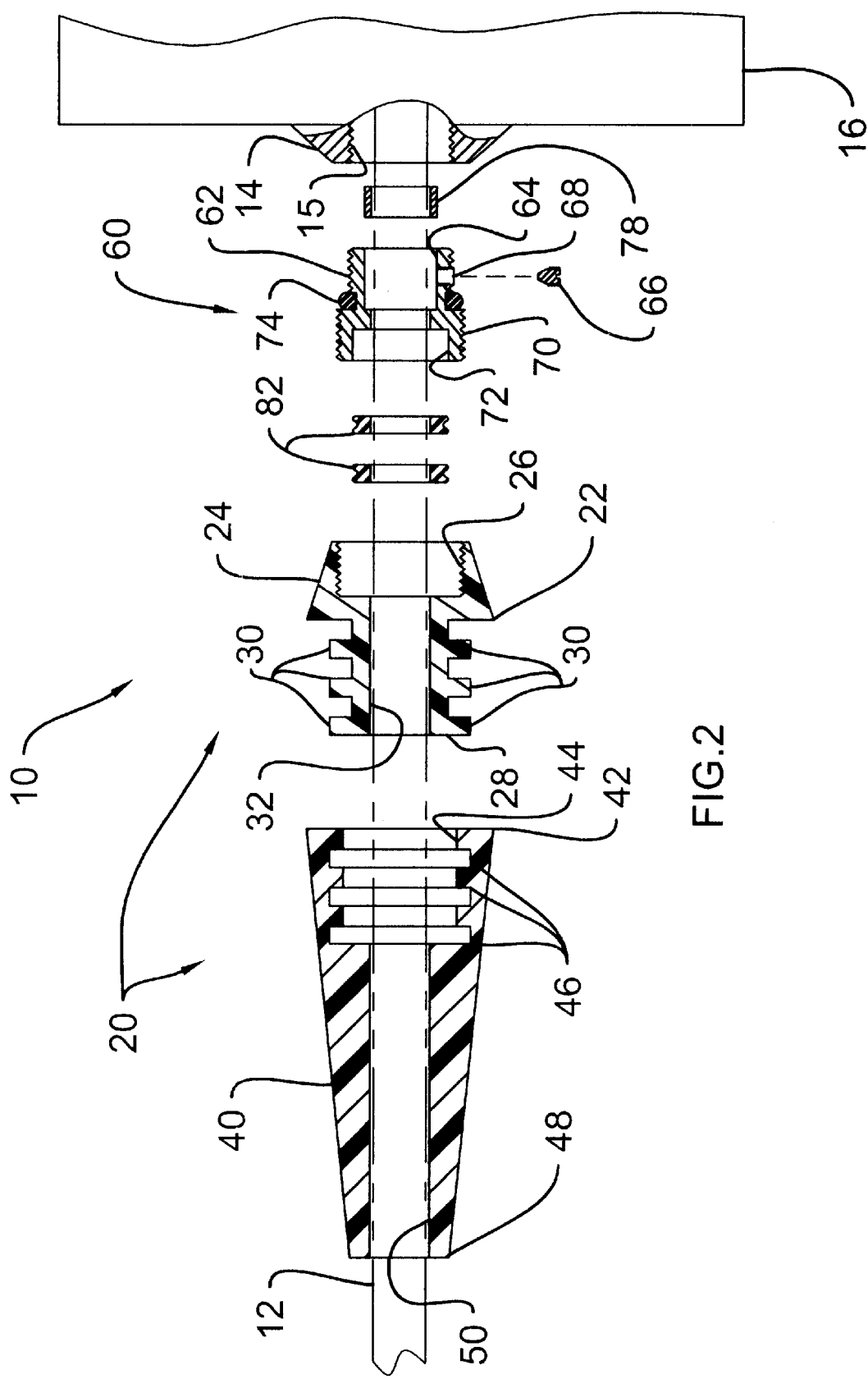
FIG. 2 is an exploded sectional view of the hermetic cable sealing of the present invention.

As best illustrated in FIG. 2, the cap unit 20 is adapted to internally accept the video cable 12. The cap unit 20 has a rigid elongated coupling member 22 and an elongated flexible bend relief member 40. The cap unit 20 can be made from any standard medical fitting material, but a black thermoplastic is preferred. The cosmetic appearance of the cap unit 20 provides a functional benefit in that some materials react with sterilants like stainless steel which appears silver and shiny. Black plastics are dark and are not as shiny as stainless steel. Additionally, thermoplastics do not react with sterilants.

The rigid elongate coupling member 22 has a first end 24 and a second end 28. The first end 24 preferably has a tapering tubular configuration, but other configurations can be used. The first end 24 has an internally threaded bore 26 which has a diameter greater than that of the video cable 12 and which extends into the coupling member 22 a distance less than the length of the first end and less than half the entire length of the coupling member. The diameter of the video cable 12 has range of about 0.25 millimeters to 50 millimeters. The second end 28 of the coupling member 22 has at least one rib 30 extending radially outward from the second end. The ribs 30 can have any geometric configuration, but are preferably rectangular in shape. The coupling member 22 has a longitudinal bore 32 extending from the second end 28 to the internally threaded bore 26. The diameter of the longitudinal bore 32 is configured to tightly accept the video cable 12 and can vary in accordance with the outer diameter of the video cable.

Figure 4:
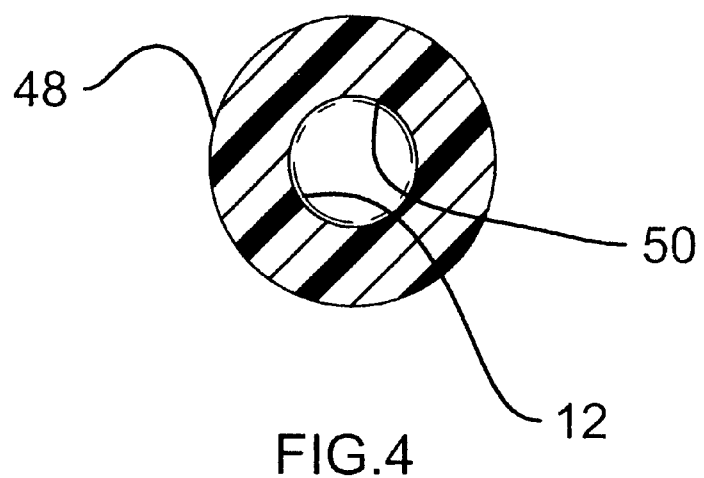
FIG. 4 is a cross sectional view taken along line 4—4 in FIG. 1 of the bend relief member forming a part of the cap unit of the present invention.

The elongated flexible bend relief member 40 with a substantial tubular configuration, as illustrated best in FIG. 4, has a first end 42 and a second end 48. The first end 42 has a larger diameter than the second end 48 which thus produces a tapered configuration. The bend relief member 40 is made of a thermoplastic material which has a greater degree of flexibility than that of the thermoplastic material used for the coupling member 22. The first end 42 has a central bore 44 which extends into the bend relief member 40 for a distance equal to the length of the second end 28 of the coupling member 22. The central bore 44 has at least one internal slot 46 for retaining the ribs 30 of the coupling member 22. The number of internal slots 46 is equal to the number of ribs 30. The ribs 30 and internal slots 46 can have any geometric shape, but a rectangular configuration is preferred. The second end 48 has a longitudinal bore 50 which extends from the second end to the slotted central bore 44. The diameter of the longitudinal bore 50 of the second end 48 is configured to tightly accept the video cable 12 and can vary dimensionally in accordance with the outer diameter of the 20 video cable. The length of the bend relief member 40 is adapted to be long enough to relieve the stress of bending of the video cable 12, which thereby reduces the chances of cable failure. The flexibility of the bend relief member 40 can be altered by changing materials, length, or design. Stiffening stringers may be placed on the outer surface of the bend relief member 40 to reduce its flexibility.

Figure 3:
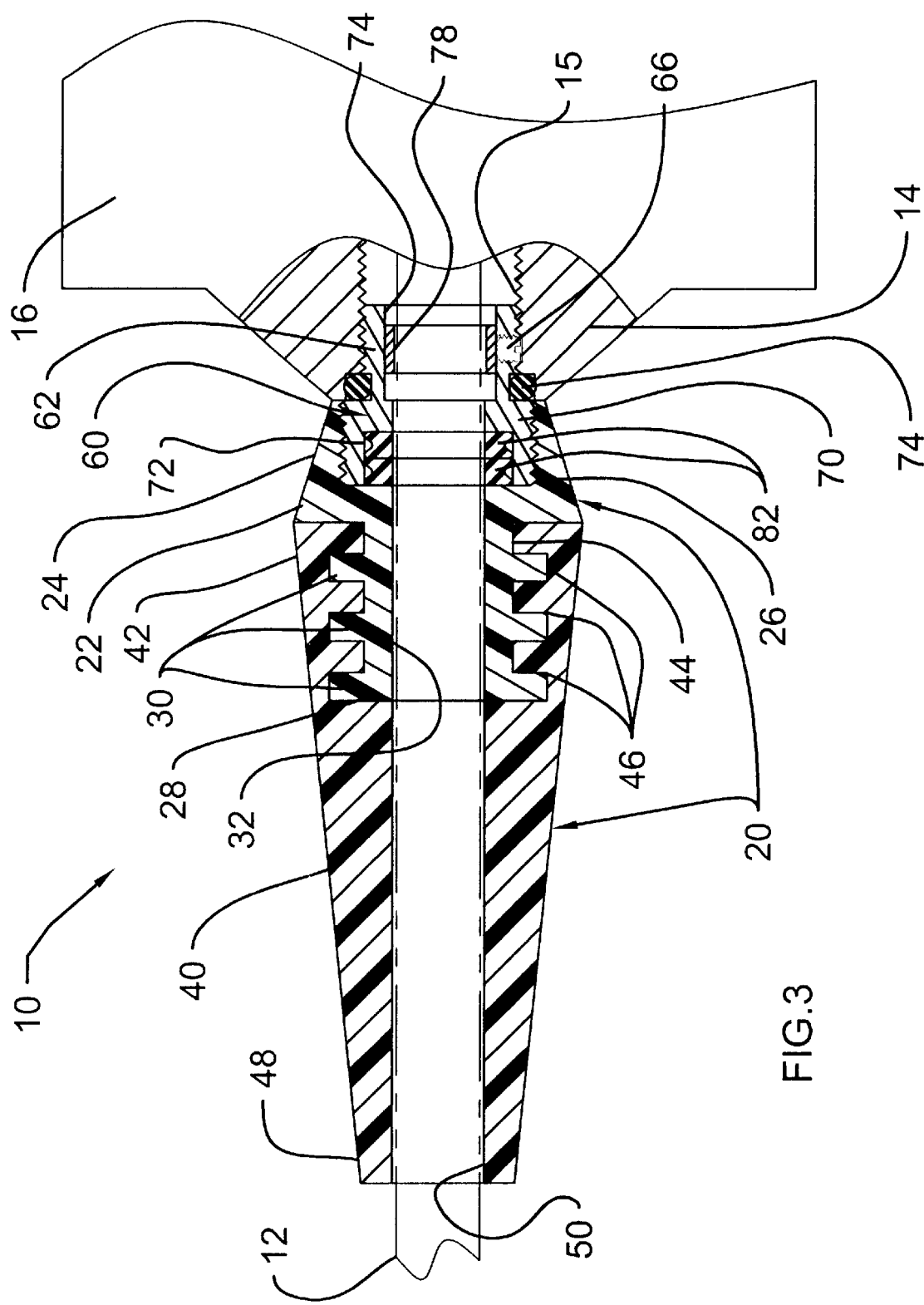
FIG. 3 is a cross sectional view taken along line 3—3 in FIG. 1 of the hermetic cable sealing system comprising the present invention.

The cap unit 20 is attached to the head shell 14 of the camera 16 by a coupler fitting 60, as best illustrated in FIGS. 2 and 3. The coupler fitting 60 has an externally threaded first end 62 and an externally threaded second end 70. The externally threaded first end 62 of the coupler fitting 60 is configured to mate with the internal threads 15 of the head shell 14 of the camera 16, and has a central bore 64. An O-ring 74 is positioned on the outer surface of the coupler fitting 60 between the first end 62 and the second end 70. When the first end 62 is threadably attached to the head shell 14 and the O-ring 74 is compressed, a hermetic seal is produced. The diameter of the central bore 64 is greater than the diameter of the video cable 12 and is adapted to accept a cable crimp 78. The cable crimp 78 increases the structural integrity of the video cable 12 attachment to the coupler fitting 60, and it does not affect the quality of the seal. Without the cable crimp 78, a user might pull the cable 12 out from the head shell 14.

Furthermore, the cable crimp 78 is secured to the first end 62 of the coupler fitting 60 by a setscrew 66. The setscrew 66 is threaded through a hole 68 in the first end 62 and secures the cable crimp 78 in position within the central bore 64 of the first end 62.

Figure 5:
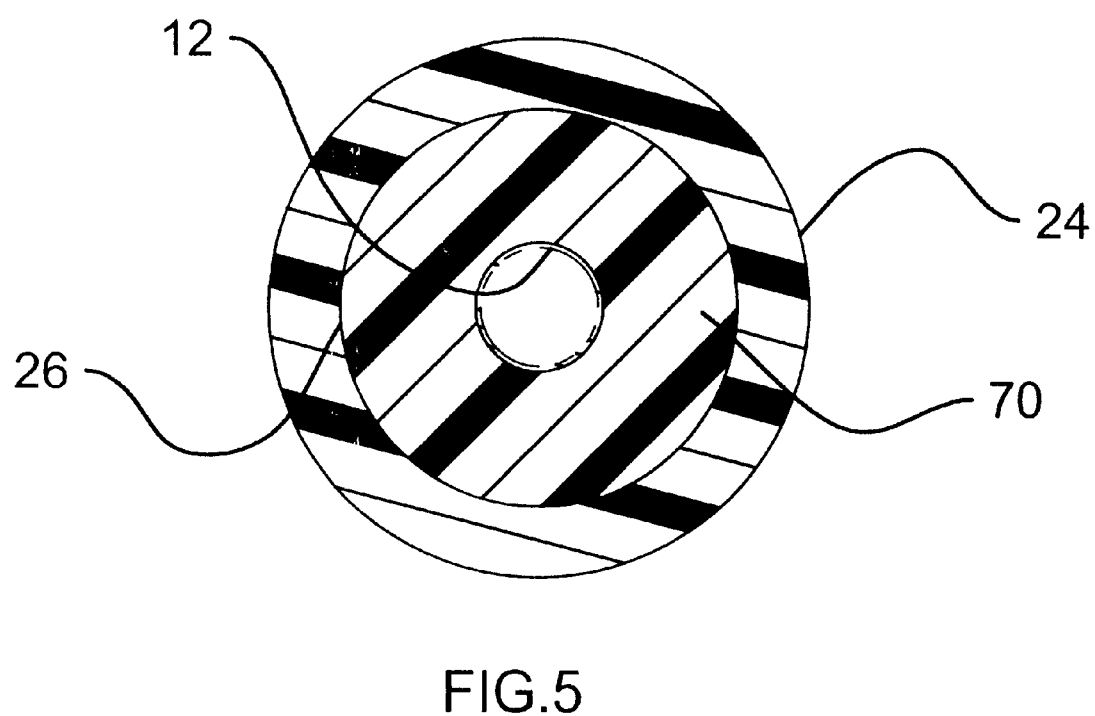
FIG. 5 is a cross sectional view taken along line 5—5 in FIG. 1 of the first end of the coupling member and the second end of the coupler fitting of the present invention.

The externally threaded, second end 70 of the coupler fitting 60 is configured to mate with the internally threaded first end 24 of the coupling member 22 of the cap unit 20, as best illustrated in FIGS. 3 and 5. The second end 70 has an internal bore 72 which is adapted to accept at least one quad ring 82, also referred to as square O-rings. A number of quad rings 82 may be used in series, but a dual ring system is preferred. The length of the bore 72 is slightly less than the width of the entire quad rings 82 used. Once the second end 70 of the coupler fitting 60 is threadably attached to the first end 24 of the coupling member 22 and the quad rings 82 are compressed therebetween, a hermetic seal is produced, as best illustrated in FIG. 3. An epoxy cement is used on the threads of the second end 70 and first end 24 so the two components do not detach. The quad rings 82 allow the components to move without loss of the hermetic seal, and the quad rings are not subject to debonding as a result of exposure to sterilants during routine sterilization of the camera 16.

In use, it can now be understood that the hermetic cable sealing system 10 is an effective and inexpensive video cable sealing system that is simple to assemble. The molded plastic cap unit 20 is manufactured by overmolding the bend relief member 40 over the coupling member 22 with the ribs 30 interlocked with the slots 46. The cap unit 20 is slid over the video cable 12 and then the quad rings 82 are slid onto the video cable after the cap unit. The video cable 12 is then passed through the coupler fitting 60 and is attached to the head shell 14 of the camera 16. The cable crimp 78 is then secured to the video cable 12 after the coupler fitting 78. The cap unit 20 is then screwed to the second end 70 of the coupler fitting 60, thereby compressing the quad rings 82 to thus produce a hermetic seal. Next, the cap unit 20 and coupler fitting 60 assembly is pushed forward so the cable crimp 78 is positioned within central bore 64 so as to be secured by the setscrew 66. Lastly, the cap unit 20 and coupler fitting 60 assembly is screwed into the internal thread 15 of the head shell 14, thereby compressing O-ring 74 and producing a hermetic seal between the cable sealing system 10 and the camera 16.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A hermetic cable sealing system comprising, in combination: a cap unit having a central bore therethrough and adapted to accept a video cable, said cap unit including:

a rigid coupling member having an internally threaded first end and a second end, said coupling member second end having at least one rib extending radially outward, said coupling member first end having a larger diameter than said coupling member second end;

an elongated flexible member having a first end and a second end, said flexible member first end having at least one internal slot for retaining said at least one rib of said coupling member, said flexible member being adapted to accept said coupling member second end, said flexible member first end having a larger diameter than said flexible member second end;

a coupler fitting adapted to mate said cap unit to a head shell of a camera and having a central bore therethrough, said coupler fitting including:

an externally threaded first end configured to mate with said head shell of said camera, said coupler fitting first end being adapted to accept a setscrew;

a cable crimp being secured around said video cable and retained in said coupler fitting first end by said setscrew;

an externally threaded second end configured to mate with said internally threaded coupling member first end of said cap unit;

at least one quad ring in said coupler fitting second end and adapted to seal said coupler fitting second end with said coupling member first end of said cap unit;

said coupling fitting first end having a smaller diameter than said coupling fitting second end; and at least one outer O-ring retained between said coupling fitting first end and said coupling fitting second end, said outer O-ring being adapted to seal said coupler fitting to said head shell of said camera.

2. A new and improved hermetic cable sealing system for mating a video cable to a camera comprising, in combination:
   a cap unit adapted to accept said video cable, said cap unit including:
      a coupling member having a first end and a second end;
      a flexible member having a first end and a second end, said flexible member first end being adapted to receive said coupling member second end;
   a coupler fitting adapted to mate said cap unit to a head shell of said camera, said coupler fitting including:
      a first end configured to mate with said head shell of said camera, said coupler fitting first end being adapted to accept a setscrew for retaining said video cable;
      a second end configured to mate with said coupling member first end of said cap unit;
      at least one quad ring in said coupler fitting second end being adapted to seal said coupler fitting second end with said coupling member first end of said cap unit; and
      at least one O-ring retained between said coupler fitting first end and said coupler fitting second end, said O-ring being adapted to seal said coupler fitting to said head shell of said camera.

3. The hermetic cable sealing system as set forth in claim 2, wherein said coupling member of said cap unit is made from a rigid thermoplastic material.

4. The hermetic cable sealing system as set forth in claim 2, wherein said first end of said coupling member has internal threads.

5. The hermetic cable sealing system as set forth in claim 4, wherein said coupler fitting second end has external threads for mating with said internal threads of said coupling member first end.

6. The hermetic cable sealing system as set forth in claim 2, and further comprising at least one rib extending radially outward from said coupling member second end.

7. The hermetic cable sealing system as set forth in claim 6, and further comprising at least one internal slot in said flexible member first end for retaining said at least one rib of said coupling member.

8. The hermetic cable sealing system as set forth in claim 2, wherein the said coupling member first end has a larger diameter than said coupling member second end.

9. The hermetic cable sealing system as set forth in claim 2, wherein said flexible member first end has a larger diameter than said flexible member second end.

10. The hermetic cable sealing system as set forth in claim 2, wherein said coupler fitting first end has external threads for mating with said head shell of said camera.

11. The hermetic cable sealing system as set forth in claim 2, and further comprising a cable crimp being secured around said video cable and retained in said coupler fitting first end by said setscrew.

12. The hermetic cable sealing system as set forth in claim 2, wherein said at least one quad ring of said coupler fitting second end is a square O-ring.

13. The hermetic cable sealing system as set forth in claim 2, wherein said coupler fitting first end has a smaller diameter than said coupler fitting second end.

* * * * *